US00PP24183P2

(12) United States Plant Patent
Bergman

(10) Patent No.: US PP24,183 P2
(45) Date of Patent: Jan. 21, 2014

(54) *CHRYSANTHEMUM* PLANT NAMED 'CIDZ0033'

(50) Latin Name: *Chrysanthemum×morifolium*
Varietal Denomination: CIDZ0033

(75) Inventor: Wendy R. Bergman, Gilroy, CA (US)

(73) Assignee: Syngenta Crop Protection AG, Basel (CH)

( * ) Notice: Subject to any disclaimer, the term of this patent is extended or adjusted under 35 U.S.C. 154(b) by 113 days.

(21) Appl. No.: 13/506,897

(22) Filed: May 23, 2012

(51) Int. Cl.
*A01H 5/00* (2006.01)

(52) U.S. Cl.
USPC ..... Plt./286

(58) Field of Classification Search
USPC ..... Plt./286, 297, 298
See application file for complete search history.

*Primary Examiner* — Howard Locker
(74) *Attorney, Agent, or Firm* — Joshua L. Price

(57) ABSTRACT

A new *Chrysanthemum* plant named 'CIDZ0033' particularly distinguished by the purple colored anemone spoon type inflorescences, strong vigorous growth with good branching, excellent flowering uniformity and a 7.5 week flowering response, with an excellent performance in high temperature growing conditions.

1 Drawing Sheet

Latin name of the genus and species of the plant claimed: *Chrysanthemum×morifolium.*

Varietal denomination: 'CIDZ0033'.

BACKGROUND OF THE NEW PLANT

The present invention comprises a new *Chrysanthemum*, botanically known as *Chrysanthemum×morifolium*, and hereinafter referred to by the variety name 'CIDZ0033'.

'CIDZ0033' is a product of a planned breeding program. The new cultivar has purple colored anemone spoon type inflorescences, strong vigorous growth with good branching, excellent flowering uniformity and a 7.5 week flowering response, with an excellent performance in high temperature growing conditions.

'CIDZ0033' originated from a hybridization made in June 2007 in a greenhouse in Bogota, Colombia. The female parent was the proprietary plant designated 'Yobaldwin', U.S. Plant Pat. No. 17,413. 'Yobaldwin' has a shorter habit, smaller inflorescence size, and a ray floret color that fades more than 'CIDZ0033'.

The male parent of 'CIDZ0033' was the proprietary plant identified as 'Yorichmond', U.S. Plant Pat. No. 19,002, with red colored single type inflorescences.

The resultant seed was sown in October 2007 in a shade structure in Fort Myers, Fla. 'CIDZ0033' was selected as one flowering plant within the progeny of the stated cross in March 2007, grown in pots under a shade structure in Fort Myers, Fla.

The first act of asexual reproduction of 'CIDZ0033' was accomplished when vegetative cuttings were propagated from the initial selection in June 2008 in a greenhouse in Fort Myers, Fla.

BRIEF SUMMARY OF INVENTION

Horticultural examination of plants grown from cuttings of the plant initiated in June 2008, and continuing thereafter, has demonstrated that the combination of characteristics as herein disclosed for 'CIDZ0033' are firmly fixed and are retained through successive generations of asexual reproduction.

'CIDZ0033' has not been observed under all possible environmental conditions. The phenotype may vary significantly with variations in environment such as temperature, light intensity, and day length.

Plant Breeder's Rights for this cultivar were applied for in Canada on Jul. 29, 2011, No. 11-7349 and in Brazil on Aug. 14, 2012, No. 218060001822012. 'CIDZ0033' has not been made publicly available more than one year prior to the filing of this application.

The following traits have been repeatedly observed and are determined to be basic characteristics of the new variety. The combination of these characteristics distinguishes this *Chrysanthemum* as a new and distinct variety.

BRIEF DESCRIPTION OF THE PHOTOGRAPHS

The accompanying photographic drawing shows typical flower and foliage characteristics of 'CIDZ0033' with colors being as true as possible with an illustration of this type.

Figure 1:
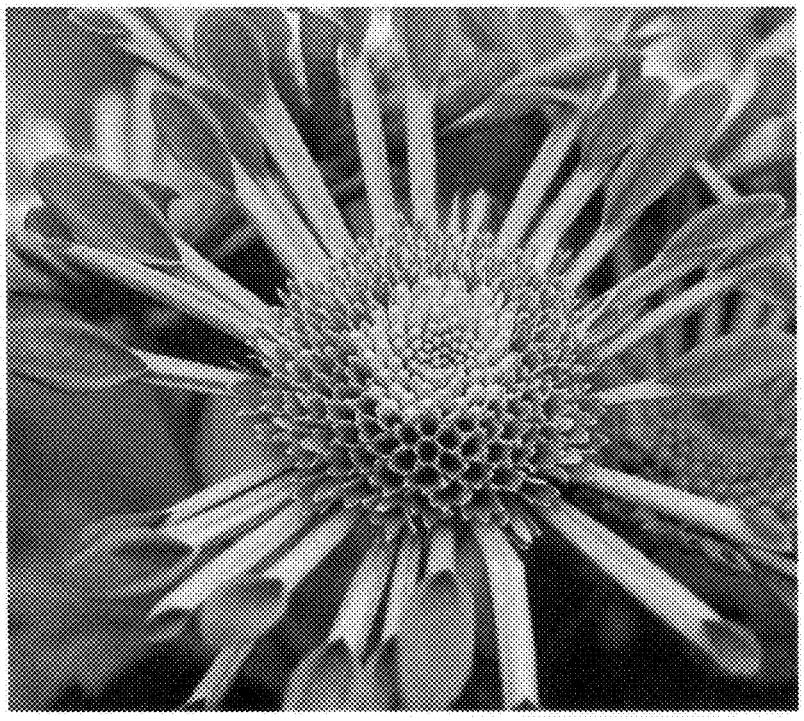
Figure 2:
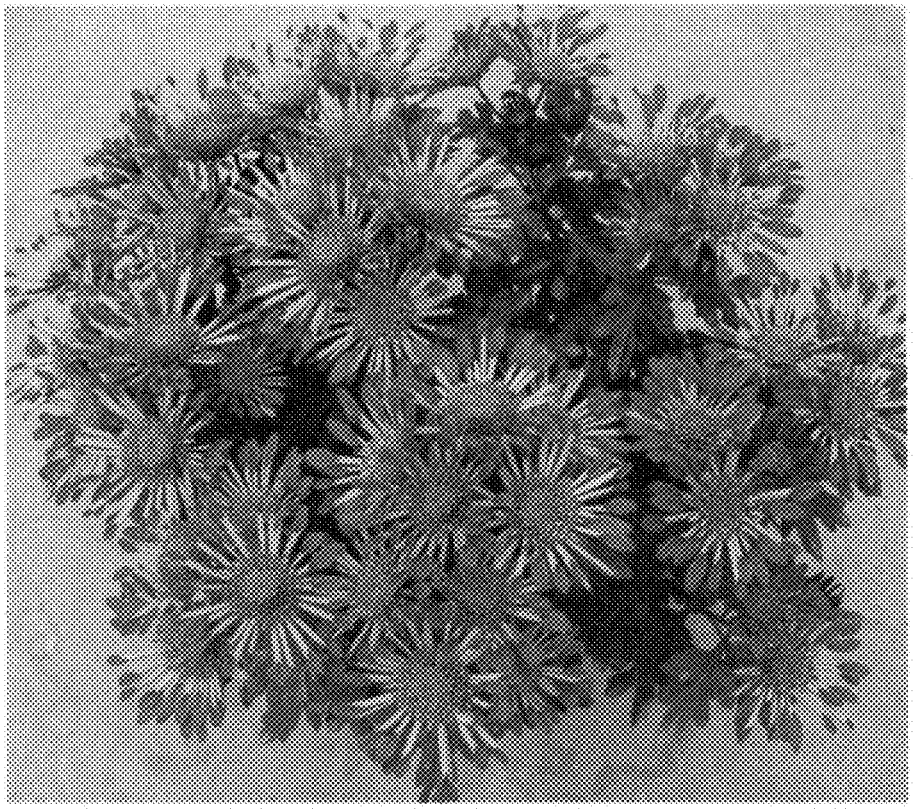

The photographic drawing shows in FIG. 1 a close-up of the inflorescences and in FIG. 2, 4 flowering plants of the new variety.

DETAILED BOTANICAL DESCRIPTION

The plant descriptions, measurements and aforementioned photographs were taken in Gilroy, Calif. in January 2012 under natural light. These plants were grown 4 plants in a 5-inch pot under center bud removal and blackcloth controlled greenhouse trial conditions in Gilroy, Calif. These plants were 10-12 weeks old.

Color references are made to The Royal Horticultural Society Colour Chart (R.H.S.) 2001.

TABLE 1

DIFFERENCES BETWEEN THE NEW VARIETY 'CIDZ0033' AND A MOST SIMILAR VARIETY

| | 'CIDZ0033' | 'CIDZ0013' (U.S. Plant Pat. No. 22,683) |
|---|---|---|
| Inflorescence type: | Anemone | Daisy |
| Growth/habit: | Fuller/wider | More upright/narrow |
| Ray floret length: | Shorter | Longer |

Plant:

*Form, growth and habit.*—Herbaceous pot-type, stems upright, freely branching, strong and moderately vigorous growth habit.

*Plant height.*—20.0-23.0 cm.

*Plant height (inflorescence included).*—27.0-30.0 cm.

*Plant width.*—21.0-26.0 cm.

Roots:

*Number of days to initiate roots.*—4 days at about 22 degrees C.

*Number of days to produce a rooted cutting.*—10-12 days at 22 degrees C.

*Type.*—Fine, fibrous, free branching.

*Color.*—RHS N155B but whiter.

Foliage:

*Arrangement.*—Alternate.

*Immature, leaf color, upper surface.*—Closest to RHS 137A.

*Lower surface.*—Between RHS 138A and RHS 138B.

*Mature, leaf color, upper surface.*—Closest to RHS 137A with some slightly darker mottling.

*Lower surface.*—Between RHS 138A and RHS 138B.

*Length.*—6.0-7.3 cm.

*Width.*—5.2-6.0 cm.

*Shape.*—Ovate.

*Base shape.*—Attenuate.

*Apex shape.*—Mucronulate.

*Margin.*—Palmately lobed; irregularly incised, somewhat serrate.

*Texture, upper surface.*—Bifid T-shaped hairs.

*Texture, lower surface.*—Bifid T-shaped hairs.

*Color of veins, upper surface.*—RHS 144C becoming indistinct.

*Color of veins, lower surface.*—RHS 144C.

*Pattern of veining.*—Palmate.

*Petiole color.*—RHS 144C.

*Petiole length.*—2.5-3.3 cm.

*Petiole diameter.*—0.2-0.25 cm.

*Petiole texture.*—Bifid T-shaped hairs.

Stem:

*Quantity of main branches per plant.*—3-5.

*Color of stem.*—RHS 146A.

*Length of stem.*—About 20.0 cm.

*Diameter.*—0.4-0.5 cm.

*Length of internodes.*—0.7-1.1 cm.

*Texture.*—Bifid T-shaped hairs.

*Color of peduncle.*—RHS 146A.

*Length of peduncle.*—4.0-6.5 cm.

*Peduncle diameter.*—0.2 cm.

*Texture.*—Bifid T-shaped hairs.

Inflorescence:

*Type.*—Compositae type, solitary spoon-type inflorescences borne terminally above foliage, ray florets arranged acropetally on a capitulum.

*Quantity of short days to flowering (response time).*—7.5 weeks.

*Natural season flowering.*—Not determined on this variety.

*Quantity of inflorescences per plant.*—10-27.

*Lastingness of individual blooms on the plant.*—4 weeks.

*Fragrance.*—Slightly spicy.

Bud (just when opening/showing color):

*Color.*—Closest to RHS N77B.

*Length.*—1.3-1.5 cm.

*Width.*—1.5 cm.

*Shape.*—Oblate.

Immature inflorescence:

*Diameter.*—6.0-7.0 cm.

*Color of ray florets, upper surface.*—Closest to RHS N79C but a little deeper.

*Lower surface.*—Closest to RHS N77B.

Mature inflorescence:

*Diameter.*—9.5-10.0 cm.

*Depth.*—2.5-2.7 cm.

*Total diameter of disc.*—3.5 cm.

*Receptacle color.*—RHS 144B.

*Receptacle height.*—0.4 cm.

*Receptacle diameter.*—0.6-0.7 cm.

Ray florets:

*Average quantity of florets.*—25-30 in 1 whorl.

*Color of florets, upper surface.*—Closest to RHS N79C.

*Lower surface.*—Closest to N77B.

*Length.*—3.7-4.0 cm.

*Width.*—0.45-0.6 cm.

*Shape.*—Long narrow spoon.

*Apex shape.*—Praemorse.

*Margin.*—Entire.

*Texture, upper surface.*—Papillose.

*Lower surface.*—Papillose.

Disc florets:

*Average quantity of florets.*—150-170.

*Color of florets.*—RHS 7B basally fading to more RHS 155D with a RHS 7B apex.

*Length.*—1.0-1.6 cm.

*Width.*—0.15-0.3 cm when open.

*Shape.*—Tubular, elongated.

*Apex shape.*—Acute, 5 pointed.

Phyllaries:

*Quantity.*—About 20.

*Color, upper surface.*—Lighter than RHS 138B.

*Lower surface.*—RHS 138B.

*Length.*—0.5-0.7 cm.

*Width.*—0.15-0.2 cm.

*Shape.*—Lanceolate.

*Apex shape.*—Acute.

*Base.*—Fused.

*Margins.*—Entire; slightly papery.

*Texture, upper surface.*—Glabrous.

*Lower surface.*—Bifid T-shaped hairs.

Reproductive organs:

*Pistil.*—1, found on both types of florets.

*Pistil length.*—0.6 cm.

*Style color.*—RHS 155C.

*Style length.*—0.45 cm.

*Stigma color.*—RHS 17C.

*Stigma shape.*—Bi-parted.

*Ovary color.*—RHS 155C but more translucent.

*Stamens.*—4, found on only on the disc florets.

*Color of filaments.*—RHS 155C.
*Length filaments.*—0.4-0.5 cm.
*Anther color.*—RHS 15A.
*Anther length.*—0.15 cm.
*Anther shape.*—Oval.
*Color of pollen.*—RHS 17B.
*Pollen amount.*—Abundant.
*Fertility/seed set.*—Has not been observed to date.
*Disease/pest resistance.*—Has not been observed to date.

What is claimed is:

1. A new and distinct variety of *Chrysanthemum* plant named 'CIDZ0033' substantially as illustrated and described herein.

* * * * *